United States Patent [19]

Kim et al.

[11] 4,266,085

[45] May 5, 1981

[54] OLEFIN DISPROPORTIONATION PROCESS

[75] Inventors: Leo Kim, Modesto, Calif.; Timm E. Paxson, Houston; Sunny C. Tang, Katy, both of Tex.

[73] Assignee: Shell Oil Company, Houston, Tex.

[21] Appl. No.: 148,099

[22] Filed: May 9, 1980

Related U.S. Application Data

[60] Continuation-in-part of Ser. No. 66,352, Aug. 13, 1979, abandoned, which is a continuation-in-part of Ser. No. 54,775, Jul. 5, 1979, abandoned, which is a division of Ser. No. 861,916, Dec. 19, 1977, Pat. No. 4,179,403.

[51] Int. Cl.$^3$ ............................................. C07C 6/00
[52] U.S. Cl. .................................. 585/645; 585/646; 585/647; 252/431 C; 252/431 N; 252/431 R
[58] Field of Search ................ 585/643, 645, 646, 647

[56] References Cited

U.S. PATENT DOCUMENTS

| | | | |
|---|---|---|---|
| 3,558,518 | 1/1971 | Zuech | 585/645 |
| 3,668,146 | 6/1972 | Ruhle | 585/643 |
| 3,689,433 | 9/1972 | Kroll | 585/646 |
| 3,691,095 | 9/1972 | Kroll | 585/647 |
| 3,725,305 | 4/1973 | Wilkonson | 585/646 |
| 3,778,385 | 12/1973 | Zuech | 585/646 |
| 3,804,870 | 4/1974 | Hughes | 585/643 |
| 3,849,513 | 11/1974 | Doyle | 585/643 |
| 3,865,892 | 2/1975 | Zuech | 585/646 |

Primary Examiner—Brian E. Hearn

[57] ABSTRACT

The disproportionation of olefins is effected by contacting the olefin with an activator and a catalyst comprising an ion exchange resin and an organic linking compound having at least one resin-compatible moiety ionically bonded to said resin and further having at least one metal complexible moiety selected from the group consisting of trivalent nitrogen, trivalent phosphorus, trivalent arsenic, trivalent bismuth and trivalent antimony complexed to a metal selected from the group consisting of molybdenum, tungsten and rhenium.

13 Claims, No Drawings

OLEFIN DISPROPORTIONATION PROCESS

This application is a continuation-in-part of copending application Ser. No. 066,352, filed Aug. 13, 1979, now abandoned, which is a continuation-in-part of copending application Ser. No. 054,775 filed July 5, 1979, now abandoned, which is a divisional of copending application Ser. No. 861,916 filed Dec. 19, 1977, which issued as U.S. Pat. No. 4,179,403 on Dec. 18, 1979.

BACKGROUND OF THE INVENTION

1. Field of the Invention

This invention relates to a process for disproportionating olefins using an activator and a catalyst comprising an ion exchange resin with a ligand ionically bonded thereto and with the ligand coordinately bonded to a transition element, particularly molybdenum, tungsten or rhenium.

2. Background

The use of heterogeneous catalysts over homogeneous catalysts has several advantages such as allowing the use of fixed beds, ease of separation of catalyst from the product and catalyst recovery and regeneration.

Traditionally, to produce heterogeneous catalysts from metals of the transition element series, these metals have been deposited on inert supports such as alumina or silica. More recently metal catalysts have been covalently attached to inert resin backbones by use of diphenylphosphine or other ligands which are attached directly to the polymer and coordinately bonded to the metal. Typical examples of this type are found in U.S. Pat. No. 3,998,864, issued Dec. 21, 1976, and in Pittman et al, *Chemtech*, p. 560–566, 1973.

In the composition utilized in the process of the invention, on the other hand, the metal is coordinately bound to a ligand and the ligand is ionically bound to an ion exchange resin. Some of the advantages of utilizing these materials in the process of the invention are that the materials are relatively simple to prepare using commercially available compounds, the preparations involve no exotic conditions, and often times may be carried out in an aqueous solvent system and the resins may be easily stripped of metal and ligands for isolation of the metal species and regeneration of the catalyst. The resin based catalysts of this invention have unique selectivity-reactivity properties when compared to their homogeneous analogues.

SUMMARY OF THE INVENTION

This invention provides a process for disproportionating olefins which comprises contacting at a temperature of between about −20° C. to +150° C. and a pressure between about 0 and 2000 psig, an olefinic hydrocarbon feedstock capable of undergoing a disproportionation process with an activator and a novel disproportionation catalyst comprising (a) an ion exchange resin, (b) a metal selected from the group consisting of molybdenum, tungsten and rhenium and, (c) a linking compound which has at least one moiety coordinately bonded to the metal and further has at least one moiety which is ionically bonded to the ion exchange resin. A suitable activator comprises a compound selected from the group consisting of compounds having the general formula $r_v T g_w$ wherein r is independently selected from the group consisting of hydrogen, hydrocarbyl radicals, and the halogenated and oxygenated derivatives thereof, said activator containing up to 30 carbon atoms, T is selected from the group consisting of Group I to III and IVA metals, g is a halogen radical, v is an integer of from 0 to 4, and w is an integer of from 0 to 4, v and w having a total equal to the valence of T. The catalyst can be easily stripped of its expensive metal component and readily regenerated for future use.

DESCRIPTION OF THE PREFERRED EMBODIMENTS

The Olefin Disproportionation Reaction

The "olefin disproportionation reaction", as defined herein can be visualized as comprising the breaking of 2 existing unsaturated bonds between first and second carbon atoms and between third and fourth carbon atoms, respectively, and the formation of 2 new unsaturated bonds between said first and third and between said second and fourth carbon atoms. Said first and second carbon atoms and said third and fourth carbon atoms can be in the same or different molecules.

The olefin disproportionation reaction is illustrated by the following reactions:

1. The disproportionation of an acyclic mono- or polyene having at least 3 carbon atoms into other acyclic mono or polyenes of both higher and lower number of carbon atoms; for example, the disproportionation of propylene yields ethylene and butenes; the disproportionation of 1,5-hexadiene yields ethylene and 1,5,9-decatriene;

2. The conversion of an acyclic mono or polyene having 3 or more carbon atoms and a different acyclic mono or polyene having 3 or more carbon atoms to produce different acyclic olefins; for example, the conversion of propylene and isobutylene yields ethylene and isopentene;

3. The conversion of ethylene and an internal acyclic mono- or polyene having 4 or more carbon atoms to produce other olefins having a lower number of carbon atoms than that of the acyclic mono- or polyene; for example, the conversion of ethylene and 4-methylpentene-2 yields 3-methylbutene-1 and propylene;

4. The conversion of ethylene or an acylic mono- or polyene having 3 or more carbon atoms and a cylic mono- or cyclic polyene to produce an acyclic polyene having a higher number of carbon atoms than that of any of the starting materials; for example, the conversion of cyclooctene and 2-pentene yields, 2,10-tridecadiene; the conversion of 1,5-cyclooctadiene and ethylene yields 1,5,9-decatriene;

5. The conversion of one or more cyclic mono- or cyclic polyenes to produce a cyclic polyene having a higher number of carbon atoms than any of the starting materials; for example, the conversion of cyclopentene yields 1,6-cyclodecadiene and continued reaction can give higher molecular weight materials;

6. The conversion of an acyclic polyene having at least 7 carbon atoms and having at least 5 carbon atoms between any 2 double bonds to produce acyclic and cyclic mono- and polyenes having a lower number of carbon atoms than that of the feed; for example, the conversion of 1,7-octadiene yields cyclohexene and ethylene; or 7. The conversion of 1 or more acyclic polyenes having at least 3 carbon atoms between any 2 double bonds to produce acyclic and cyclic mono- and polyenes generally having both a high and lower number of carbon atoms than that of the feed material; for example, the conversion of 1,4-pentadiene yields, 1,4-cyclohexadiene and ethylene.

Olefins applicable for use in the process of the invention are non-tertiary, nonconjugated acyclic mono- and polyenes having at least 3 carbon atoms per molecule including cycloalkyl, cycloalkenyl, and aryl derivatives thereof; cyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 2–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least 1 hydrogen atom.

A preferred feed olefin hydrocarbon is 1. a nontertiary, nonconjugated acyclic mono- or polyene having at least three carbon atoms per molecule including cycloalkyl, cycloalkenyl, and aryl derivatives thereof;
2. cyclic mono- or polyenes having at least four carbon atoms per molecule including alkyl and aryl derivatives thereof;
3. mixtures of (1) and (2); or
4. mixtures of ethylene and groups (1) and/or (2).

The conditions under which the olefins react may vary with the composition of the feed and the desired products. Reaction temperatures may range from $-20°$ to $+150°$ C., temperatures in the range of 20° to 100° C. being preferred.

Reaction pressures may be in the range 0 to 2000 psig.

In a continuous process, reaction times may vary between 0.01 second and 120 minutes, preferably between 0.1 second and 10 minutes.

In a batch process, suitable olefin/catalyst weight ratios are in the range 1000:1 to 1:1.

If desired, the process may be carried out in the presence of an inert diluent, for example paraffinic or cycloparaffinic hydrocarbons.

The Catalyst Preparation

The ion exchange resins utilized to prepare the composition utilized in this invention are well known in the art and are readily available commercially. These are in the gel form or are macroporous and are either strongly acidic, weakly acidic, strongly basic, intermediate basic, weakly basic or mixed acid-base. The strong acid resins typically have base resins of cross-linked styrene, styrene divinylbenzene, phenol-formaldehydes, benzene-formaldehyde, having functional sulfonic or phosphonic acid groups attached thereto. Also suitable are the fluorinated alkyl sulfonic acid resins containing the $-CFSO_3H$ group as, for example, the NAFION® type resins supplied by E. I. DuPont De Nemours. The weak acid resins are those with carboxylic acid groups and are typically acrylic acid derivatives such as, for example, those resins prepared by the copolymerization of methacrylic acid and divinylbenzene. Another weak acid resin is the chelating type which is a styrene-divinylbenzene copolymer containing aminodiacetic acid functional groups which can serve as an anion exchanger at very low pH. The basic resins typically have base resins of cross-linked styrene, styrene-divinylbenzene, phenol-formaldehydes, benzene-formaldehyde, epoxypolyamine, phenolic-polyamine having functional amine, either primary, secondary, tertiary or quaternary, or pyridinium groups attached thereto. Typical examples of suitable commercially supplied resins are given in Table I (reference: Bio-Rad Laboratories Catalogue, Chromatography, Electrophoresis, Immunochemistry and Membrane Filtration, Price List C, March 1977, p. 11).

The preferred resin choice for the composition used in this invention will depend on the particular ionically bondable moiety utilized on the linking compound as well as on the particular use envisioned for the composition. For example, if the composition were used in liquid-phase catalysis, the composition and pH of the liquid would determine the preferred resin to be utilized.

The linking compound is hydrocarbyl, i.e., alkyl, aryl, or mixtures or aryl and alkyl components, which can be either cyclic or acyclic or mixtures thereof containing from 1 to about 100 carbon atoms, preferably from about 3 to about 80 carbon atoms and has at least two moieties containing an atom other than carbon.

At least one moiety is in the ionic or ionizable form and is compatible with the exchange group on the ion exchange resin, i.e., when the exchange group is acidic the resin compatible ionic moiety on the linking compound is basic-derived and vice versa. The acidic-derived resin compatible ion moiety is derived from carboxylic acid ($RCO_2^-$), phosphonic acid ($RPO(OH)O^-$), phosphinic acid ($R_2POO^-$), sulfenic acid ($RSO^-$), sulfinic acid ($RSOO^-$), sulfonic acid ($RSO_2O^-$), boronic acid ($RB(OH)O^-$), boronous acid ($RBO^-$). The basic-derived resin compatible ion moiety is monohydrocarbyl ammonium ($RN^+H_3$), dihydrocarbyl ammonium ($R_2N^+H_2$), trihydrocarbyl ammonium ($R_3N^+H$), quarternary ammonium ($R_4N^+$), pyridinium ($RC_5H_4N^+R_1$), phosphonium ($R_4P^+$), arsonium ($R_4As^+$), and sulfonium ($R_3S^+$).

The linking compound may have more than one of the ionic moieties. It may be polyfunctional, for example, in carboxylate ion, in phosphonate ion, in sulfonate ion, in quaternary ammonium ion, in pyridinium and the like. The polyfunctional group may be the same or different.

At least one other moiety of the linking compound has an atom capable of complexing with metals from the transition element series, and consists of trivalent nitrogen, trivalent phosphorus, trivalent arsenic, trivalent bismuth, and trivalent antimony.

TABLE I

| Type and Exchange Group | Bio-Rad | Dow Chem. Company "Dowex" | Diamond Shamrock "Duolite" | Rohm & Haas Co. "Amberlite" | Permutit Company (England) | Permutit Company (U.S.A.) |
|---|---|---|---|---|---|---|
| Anion exchange resins | | | | | | |
| Strongly Basic, polystyrene | AG 1-X1 | 1-X1 | | | DeAcidite FF | S-100 |
| $\phi-CH_2N^+(CH_3)_3Cl^-$ | AG 1-X2 | 1-X2 | | | (lightly | |
| | AG 1-X4 | 1-X4 | A-101D | IRA-401 | crosslinked) | |
| | AG 1-X8 | 1-X8 | | IRA-400 CG 400 | DeAcidite FF | |
| | AG 1-X10 | 1-X10 | | IRA-425 | | |
| | AG 21K | 21K | | IRA-402 | | |

TABLE I-continued

| Type and Exchange Group | Bio-Rad | Dow Chem. Company "Dowex" | Diamond Shamrock "Duolite" | Rohm & Haas Co. "Amberlite" | Permutit Company (England) | Permutit Company (U.S.A.) |
|---|---|---|---|---|---|---|
| $\phi-CH_2N^+(CH_3)_2(C_2H_4OH)\ Cl^-$ 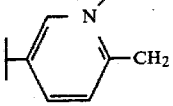 | AG 2-X4 AG 2-X8 AG 2-X10 Bio-Rex 9 | 2-X4 2-X8 | A-102D | IRA-410 | | S-200 A-580 |
| Intermediate Base, epoxypolyamine $R-N^+(CH_3)_2Cl^-$ and $R-N^+(CH_3)_2(C_2H_4OH)\ Cl^-$ | Bio-Rex 5 | | A-30B | | F | S-310 S-380 |
| Weakly Basic, polystyrene or phenolic polyamine $\phi-CH_2N^+(R)_2Cl^-$ | AG 3-X4A | WGR | A-6 A-7 A-4F | IR-45 IR-4B IRA-68 | G | S-300 S-350 |
| Cation exchange resins | | | | | | |
| Strong Acidic, phenolic $R-CH_2SO;\ H^+$ | Bio-Rex 40 | | C-3 | | Zeocarb 215 | |
| Strong Acidic, polystyrene $\phi-SO_3^-H^+$ | AG 50W-X1 AG 50W-X2 AG 50W-X4 AG 50W-X8 AG 50W-X10 AG 50W-X12 AG 50W-X16 | 50W-X1 50W-X2 50W-X4 50W-X8 50W-X10 50W-X12 50W-X16 | C20 C-20X10 C-20X12 | IR-116 IR-118 IR-120 CG-120 IR-122 IR-124 | Zeocarb 225 (X4) Zeocarb 225 | Permutit Q Q-100 Q-110 Q-130 |
| Weakly Acidic, acrylic $R-COO^-Na^+$ | Bio-Rex 70 | | CC-3 | IRC-50 CG-50 | Zeocarb 226 | Q-210 |
| Weakly Acidic chelating resin polystyrene 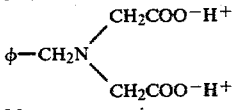 | Chelex 100 | A-1 | | | | |
| Macroporous resins | | | | | | |
| Strong Base, polystyrene $\phi-CH_2N^+(CH_3)_3\ Cl^-$ | AG MP-1 | MSA-1 | A-161 | IRA-900 | | |
| Strong Acid, polystyrene $\phi-SO_3^-\ H^+$ | AG MP-50 | MSC-1 | C-25D | 200 | | |
| Mixed bed resins | | | | | | |
| $\phi-SO_3^-H^+$ & $\phi-CH_2N^+(CH_3)_3OH^-$ | AG 501-X8 | | GPM-331 G | MB-1 | Bio-Demineralit | M-100 |

The three valences of the complexing atoms may be satisfied by any organic radical; saturated or unsaturated aliphatic, and/or saturated or unsaturated heterocyclic and/or aromatic radicals. These radicals may contain any functional group such as carbonyl, nitro, and hydroxy groups as well as saturated and unsaturated alkyl groups and the radical may be bonded to the complexing atom directly through a carbon-complexing atom linkage or through an electronegative atom such as oxygen or sulfur.

It is also suitable for a simple organic radical to satisfy more than one of the valences of the complexing atoms, thereby forming a heterocyclic compound with the trivalent complexing atom. For example, an alkylene radical may satisfy two of the valences thereby forming a cyclic compound. Another example would be the alkylene dioxy radical to form a cyclic compound where oxygen atoms link an alkylene radical to the complexing atom. In these two examples the third valence may be satisfied by any other organic radical.

The linking compound may have more than one of the metal-complexing moieties. It may be, for example, polydentate in phosphorus atom, e.g., it may be bi- or tridentate, having two or three phosphorus atoms. It may have mixed complexing atoms, e.g., a phosphorus and arsenic atom or two phosphorus atoms and one nitrogen atom, etc.

The trivalent nitrogen atom will be present as an amine, i.e., as a primary, secondary, tertiary, quaternary amine or as pyridine or cyanide. The trivalent phosphorus will be present as phosphine ($R_3P$), phosphinite ($ROPR_2$), phosphonite ($(RO)_2PR$) and phosphite ($(RO)_3P$). Correspondingly, trivalent arsenic will be available as arsine, arsinite, arsonite and arsenite, trivalent bismuth as bismuthine, bismuthinite, bismuthonite and bismuthite; and trivalent antimony as stibine, stibinite, stibonite and stibite. The preferred complexing atoms are phosphorus and nitrogen. The tertiary amines, phosphines, arsines and stibines and bismuthines have a marked tendency to form nonionic complexes with metals.

When the linking compound is polydentate in an ionizable heteroatom, it is understood that there will be a statistical distribution of the ionized atoms upon quaternization or protonation. For example, if one mole of a linking compound which contains 3 amine groups is protonated with 2 moles of HCl, then some of the molecules of the linking compound will have 3 quaternized amine groups, some will have 2 and some will have 1, but on the average there will be 2 quaternized amine groups per molecule. It is further understood from general principles of organic chemistry that unit charges resulting from quaternization and protonation can be distributed as partial charges over several heteroatoms in a linking compound molecule.

Thus the linking compound as reacted in the composition used in this invention will have at least one protonized or quaternized heteroatom and at least one heteroatom complexed with a transition element metal. Suitable linking compounds utilized in making the composition used in the invention include but are not limited to the following examples:
tris(dimethylamino)phosphine
tris(diethylamino)phosphine
tris(diisopropylamino)phosphine
tris(methylethylamino)phosphine
tris(p-dimethylaminophenyl)phosphine
tris(p-diethylaminophenyl)phosphine
tris(p-methylethylaminophenyl)phosphine
tris(o-dimethylaminophenyl)phosphine
tris(m-dimethylaminophenyl)phosphine
tris(dimethylaminoethyl)phosphine
tris(dimethylaminoethyl)phosphite
ethylbis(diphenylphosphinoethyl)amine.

Substitution of phosphinites, phosphonites, phosphites for the phosphine in the above compounds as well as arsines, arsinites, arsonites, arsenites, bismuthenes, bismuthinites, bismuthonites, bismuthites, stibines, stibinites, stibonites, stibites and amines produces linking compounds useful in preparing the composition used in this invention. Other suitable compounds are:
tris(4-N,N-dimethylaminophenyl)phosphine
2-(P,P-diphenylphosphino)benzoic acid
tris(beta-aminoethyl)amine
2-chloronicotinic acid, and 2-carboxypyridine
1,1-dimethyl-4-phenyl piperazinium salt
2,2′-alkylarsino-1,1′-diphenylamine
2-(P,P-dicyclohexylphosphino)benzoic acid
beta-(dicyclohexylphosphino)pripionic acid
1,4-(P,P-diphenylphosphino)benzene
2-diphenylphosphino-3-carboxy-2-butene
2-(P,P-diphenylphosphino)benzene sulfonic acid
2-amino-s-triazine
1-diphenylphosphino-2-diphenylphosphinoethane
tris-(beta-N,N-diarylaminoethyl)phosphite
tris(N,N-diarylamino)phosphine
bis(beta-diphenylphosphinoethyl)ethylamine
3-(dialkylphosphino)benzene phosphonic acid.

Thus the organic linking compound is hydrocarbyl with at least one moiety capable of coordinate bonding and at least one moiety capable of ionic bonding. The primary limitation on the organic linking compound is a functional use, i.e., one moiety must be capable of coordinate bonding and the other moiety must be capable of ionic bonding. These moieties are well known to those skilled in the art.

The metals complexed with the linking compound are selected from the group consisting of molybdenum tungsten and rhenium.

The complexed metals can be in various oxidation states. See "Complexes of the Transition Metals with Phosphines, Arsines and Stibines", by G. Booth, Adv. Inorg. Nucl. Chem. 6, 1–69 (1964) for a comprehensive description of complexes. For example, the Booth reference cites the following oxidation states for metals complexed with phosphines.

TABLE II

| Metal | Oxidation State for Stable Phosphine Complexes |
|---|---|
| Mo | 0, 1, 2, 3, 4 |
| W | 0, 1, 2, 3, 4 |
| Re | 0, 1, 2, 3, 4, 5 |

Articles dealing with the complexing of amines with metals are "Inorganic Complexes", Jorgensen, C. K., Academic Press 1963, chap. 4 and "Chemistry Coordination Compounds", Bailer (Ed.), Am. Chem. Soc. Monograph Series 131, 1956. The above references cite the following oxidation states for metals complexed with amines.

TABLE III

| Metal | Oxidation State of Stable Amine Complexes |
|---|---|
| Mo | 0, 3 |
| W | 2 and 3 (polynuclear), 4 (mononuclear) |
| Re | 3, 5 |

The composition used in the invention may have more than one transition element metal present. The composition may also have the metal(s) co-complexed with other ligands in addition to the linking compound. For example, from the above-noted Booth reference the metal complexed moiety of the composition could have the following form and still be within the scope of the invention, i.e., $M_Y \quad M_{Z'} \quad O_A \quad H_B \quad X_C$ $(CN^-)_D(CO)_E(NO)_F(Cp)_G(Py)_H(Acac)_I(AsR_3)_J(NR_3)_K(PR_3)_L(SnX_3^-)_M(GeX_3^-)_M(Carb)_NP_Q$ $M_Y$ = metal in oxidation state shown in Table II or Table III Y=0 to n mononuclear to polynuclear cluster $M_{Z'}$ = metal in oxidation state shown in Table II or Table III Z=0 to n mononuclear or mixed metal polynuclear cluster where n is an integer greater than 0 when Y>0 and Z>0

O = oxygen where A=0 to n

H = hydrogen where B=0 to n

X = halide F, Cl, Br, I; where C=0 to 5

$(CN^-)$ = cyanide where D=0 to 5 when y+z=1 or D=1 to n when y+x>1

(CO) = carbonyl where E=0 to 5 when y+z=1 or E=1 to n when y+z>1

(NO) = nitrosyl where F=0 to 5 when y+z=1 or E=1 to n when y+z>1

Cp = cyclopentadienyl where G=0 to 3 when w=z=1 or G=1 to n when y+z>1

Py = pyridine where H=0 to 5 when y+z=1 or H=1 to n when y+z>1

Acac = acetylacetonate where I=0 to 3 when y+z=1 or I=1 to n when y+z>1

$(AsR_3)$ = arsines, where R=H, alkyl or aryl and J=0 to 5 when y+z=1 or J=1 to n when y+z>1 the arsine also may be of the chelating type or contain mixed donating atoms e.g.

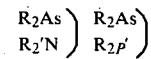

$(NR_3)$ = amines, where R=H, alkyl, or aryl and K=0 to 5 when y+z=1 or K=1 to n when y+z>1 as with arsines, a chelating or mixed donor chelating ligand may be employed.

(PR$_3$)=phosphines where R=H, alkyl, or aryl, and L=0 to 5 when y+z=1 or L=1 to n when y+z>1 as with arsines, and amines, a chelating ligand may be employed (SnX$_3^-$) or (GeX$_3^-$)=trihalostannyl or trihalogermyl where X=F, Cl, Br, I and M=0 to 5 when y+z=1 or M=1 to n when y+z>1

(Carb)=carboxylate where N=0 to 5 when y+z=1 or N=1 to n when y+z>1

P=the bridging moiety/ligand between the metal and the resin support and Q=1 to n.

In general terms this invention is a process for the production of olefins by disproportionation which comprises contacting at a temperature of between about −20° C. and +150° C. and a pressure of between about 0 and 2000 psig an olefinic hydrocarbon feedstock capable of undergoing a disproportionation process with an activator and a catalyst comprising an ion exchange resin, a metal selected from the group consisting of molybdenum, tungsten and rhenium, and an organic linking compound which has at least one moiety which is ionically bonded to said ion exchange resin and further has at least one moiety which is coordinately bonded to said metal. In particular, the process will utilize, depending on the ion exchange resin, either a catalyst comprising:

(a) an ion exchange resin having a strongly acidic, weakly acidic, or mixed acid-base type functional group;

(b) an element selected from the group consisting of molybdenum, tungsten and rhenium, and (c) an organic linking compound of from 1 to about 100 carbon atoms which has at least one moiety selected from the group consisting of monohydrocarbyl ammonium, dihydrocarbyl ammonium, trihydrocarbyl ammonium, quaternary ammonium, pyridinium and phosphonium which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said element, or a catalyst comprising:

(a) an ion exchange resin having a basic-type functional group;

(b) an element selected from the group consisting of molybdenum, tungsten and rhenium; and (c) an organic linking compound of from 1 to about 100 carbon atoms which has at least one moiety derived from the group consisting of carboxylic acid, phosphonic acid, phosphinic acid, sulfenic acid, sulfinic acid, sulfonic acid, boronic acid and boronous acid which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said element.

The catalyst of this invention is suitably used in conjunction with a conventional activator, also referred to as a co-catalyst or catalytic adjuvant. Activators have traditionally been used with both heterogeneous and homogeneous catalysts containing molybdenum, tungsten or rhenium. Although the catalysts in the process of this invention are significantly different from prior art catalysts, conventional activators may still be used. The activators are generally Lewis acids or reducing agents. Suitable activators comprise, for example, compounds selected from the group consisting of compounds having the general formula $r_v Tg_w$ wherein r is independently selected from the group consisting of hydrogen, hydrocarbyl radicals, and the halogenated and oxygenated derivatives thereof, said activator containing up to 30 carbon atoms, T is selected from the group consisting of Group I to III and IVA metals, g is a halogen radical, v is an integer of from 0 to 4, and w is an integer of from 0 to 4, v and w having a total equal to the valence of T. Illustrative of r are hydrogen-, methyl-, ethyl-, isopropyl-, n-butyl, fluoromethyl-, dichloromethyl, α,β-dichloroethyl-, and the like. Preferred metals in this regard include aluminum and tin, with aluminum being more preferred. Typical examples of activators include Al(CH$_3$CH$_2$)$_2$Cl, Al$_2$(CH$_3$)$_3$Cl$_3$, (CH$_3$)$_4$Sn and AlCl$_3$. The amount of activator used is not critical, although typically the molar ratio of activator to metal in the catalyst is from about 0.1:1 to about 50:1. The activator chosen may depend on, for example, the catalytic composition used, the feedstock or other reaction conditions. The choice and amount of activator to be used in conjunction with the composition of this invention may be readily determined by routine experimentation.

This invention, therefore, is also directed to an improved process. In a process for the production of olefins by disproportionation which comprises contacting at a temperature of between about −20° C. and +150° C. and a pressure of between about 0 and 2000 psig an olefinic hydrocarbon feedstock capable of undergoing a disproportionation process with an activator and a catalyst, the improvement comprises using a catalyst comprising an ion exchange resin, a metal selected from the group consisting of molybdenum, tungsten and rhenium, and an organic linking compound which has at least one moiety which is ionically bonded to said ion exchange resin and further has at least one moiety which is coordinately bonded to said metal.

The composition of this invention and preparation thereof is described by the following illustrative embodiments which are provided for illustration and are not construed as limiting the invention.

ILLUSTRATIVE EMBODIMENTS

The catalyst preparation procedures described below were carried out in nitrogen-filled dry boxes. The solvent benzene was purified by distillation over CaH$_2$, all other solvents were of reagent-grade and used as supplied. The metal complex Mo(NO)$_2$Cl$_2$, and compounds CH$_3$Br, SnCl$_2$.2H$_2$O, isonicotinic acid, and phosphines [(CH$_3$)N]$_3$P, [(CH$_3$)$_2$NC$_6$H$_4$]$_3$P, [(CH$_3$)$_2$NCH$_2$CH$_2$O]$_3$P were used as supplied. The quaternized aminophosphines were prepared by the reaction of 1 equivalent of CH$_3$Br with an aminophosphine in toluene solution at room temperature. The quaternized aminophosphine precipitated readily from the toluene solution. The resins are indicated by (resin backbone)-(exchange group), e.g. a sulfonated styrene divinylbenzene resin would be (styrene-divinylbenzene)-(SO$_3^-$), etc. Ph, C$_6$H$_5$ and φ are used as abbreviations for phenyl; -φ- and C$_6$H$_4$ indicates p-substitued benzene moieties.

PREPARATION OF RESIN-LINKING COMPOUND MOIETY

EXAMPLE 1

Preparation of sulfonated styrene-divinylbenzene resin/$[(CH_3)_2N]_3P$ compound.

The aminophosphine $[(CH_3)_2N]_3P$ (0.98 g, 60 mmol) was dissolved in 175 ml of acetone in a 250 ml round-bottomed flask. 5.0 Grams of Rohm and Haas XN1010H$^+$ resin (acid form; macroreticular sulfonated styrene-divinylbenzene, 3.3 meq/g) which had previously been thoroughly washed with deionized water and dried was added to the flask. The mixture was then stirred magnetically from the side of the flask for 48 hours to prevent resin attrition. The resin was filtered by suction, washed with 3×50 ml of acetone, and dried in a vacuum oven (50° C.) overnight. Analysis showed the product as having the approximate formula (styrene-divinylbenzene)-$(SO_3^-)_{1.5}[([(CH_3)_2N]_3P)\text{-}(H^+)_{1.5}]$.

EXAMPLE 2

Preparation of sulfonated styrene-divinylbenzene resin/$[(CH_3)_2NC_6H_4]_3P$ compound.

The aminophosphine $[(CH_3)_2NC_6H_4]_3P$ (14.0 g, 35.8 mmol) was dissolved in 1000 ml warm benzene, cooled to room temperature, and filtered into a 2-l round-bottomed flask quickly. 10.0 G of XN1010H$^+$ ion-exchange resin was added, and the mixture stirred magnetically on side of flask for 72 hours. The resin was then filtered, washed with benzene and vacuum dried in oven (40° C.). Analysis showed the product as having the approximate formula (styrene-divinylbenzene)-$(SO_3^-)_{1.5}[([(CH_3)_2NC_6H_4]_3P)(H^+)_{1.5}]$.

EXAMPLE 3

Preparation of sulfonated styrene-divinylbenzene resin/$[(CH_3)_2 NCH_2CH_2O]_3P$ compound.

This material was prepared in a similar manner as in Example 1 except that 3.54 g (12.0 mmol) of the aminophosphine $[(CH_3)_2NCH_2CH_2O]_3P$, 10.0 g of XN1010H$^+$ resin, and 300 ml of acetone were used. Analysis showed the product as having the approximate formula (styrene-divinylbenzene)-$(SO_3^-)_{1.5}[([(CH_3)_2NCH_2CH_2O]_3P)(H^+)_{1.5}]$.

EXAMPLE 4

Preparation of sulfonated styrene-divinylbenzene resin $[(\phi_2PCH_2CH_2)_2NCH_2CH_3]$ compound.

This material was prepared in a similar manner to Example 1 except that 2.82 g (6 mmol) of the aminophosphine $(\phi_2PCH_2CH_2)_2NCH_2CH_3$ and 200 ml of acetone was used. Analysis showed the product as having the approximate formula (styrene-divinylbenzene)-$(SO_3^-)_{1.5}[([(C_6H_5)_2PCH_2CH_2]_2NCH_2CH_3)(H^+)_{1.5}]$.

EXAMPLE 5

Preparation of sulfonated styrene-divinylbenzene resin/methylquaternized $[(CH_3)_2N]_3P$ compound.

The quaternized aminophosphine $([(CH_3)_2N]_3P)(CH_3^+)Br^-$ (7.0 g wet) was dissolved in 350 ml of deionized water in a 500 ml round-bottomed flask. 10.0 G of XN1010Na ion-exchange resin (prepared by exhaustive ion-exchange of XN1010H$^+$ with 10 l of 1 N NaCl or when the pH of the effluent wash was neutral) was added. The mixture was side-stirred for 48 hours, filtered with suction, and the resin washed with 5×100 deionized H$_2$O, then vacuum dried in oven overnight (45° C.). Analysis showed the product as having the approximate formula (styrene-divinylbenzene)-$(SO_3^-)[([(CH_3)_2N]_3P)(CH_3^+)]$.

EXAMPLE 6

Preparation of sulfonated styrene-divinyl benzene resin/methylquaternized $([(CH_3)_2NC_6H_4]_3P)$ compound.

This material was prepared in a similar manner as in Example 5 except that 10.4 (21.1 mmol) of the quaternized aminophosphine, 12.0 g of XN1010Na, and 1900 ml of an acetone/H$_2$O(12:7 v/v) solution were used. Analysis showed the product as having the approximate formula (styrene-divinylbenzene)-$(SO_3^-)$-$[([(CH_3)_2NC_6H_4]_3P)(CH_3^+)]$.

EXAMPLE 7

Preparation of sulfonated styrene-divinylbenzene resin/methylquaternized $[(CH_3)_2NCH_2CH_2O]_3P$ compound.

This material was prepared in a similar manner as in Example 5 except that 5.6 g (14.4 mmol) of the quaternized aminophosphine, 8.0 g of XN1010Na, and 400 ml of H$_2$O were used. Analysis showed the product as having the approximate formula (styrene-divinylbenzene)-$(SO_3^-)[([(CH_3)_2NCH_2CH_2O]_3P)(CH_3^+)]$.

EXAMPLE 8

Preparation of sulfonated styrene-divinylbenzene resin/methylquaternized $[([(C_6H_5)_2PCH_2CH_2]_2NCH_2CH_3)]$ compound.

This material was prepared in a similar manner as in Example 5 except that 2.0 g (3.5 mmol) of the quaterized amonophosphine, 4.0 g of XN1010Na, and 200 ml of deionized water were used. Analysis showed the product as having the approximate formula (styrene-divinylbenzene)-$(SO_3^-)[([(C_6H_5)_2PCH_2CH_2]_2NCH_2CH_3)(CH_3^+)]$.

EXAMPLE 9

Preparation of sulfonated styrene resin/$[(CH_3)_2NC_6H_4]_3P$ compound.

This material was prepared in a manner similar to Example 2 except that Dow MSC-1H resin (sulfonated polystyrene, macroreticular, 1.6 meq/g) was used. Analysis showed the product as having the approximate formula (styrene)-$(SO_3^-)_{1.5}[([(CH_3)_2NC_6H_4]_3P(H^+)_{1.5}]$.

EXAMPLE 10

Preparation of sulfonated styrene resin/methylquaternized $([(CH_3)_2NC_6H_4]_3P)$ compound.

50 Grams of the hydrogen form of BioRad AG 50W-X1 (sulfonated polystyrene, 5.0 meq/g) was placed in a course fritted glass funnel which was then Na exchanged with 1 liter of 1 N NaCl by adding the salt solution in aliquots so its slowly ran through the resin. The resin was then washed in a similar manner with 2 liters of deionized water. This was followed by an acetone rinse and the resin was dried in a vacuum oven at about 40° C. for 2 days. A 5.0 g portion of the dried Na form of the resin was then added to 2 liters of an acetone-water solution (1:1 v/v) which contained the quaternized aminophosphine (2.0 g, 4.1 mmol) and stirred overnight under N$_2$. The material was then filtered and washed with an acetone solution, a water solution and then air-dried. Analysis showed the product as having the approximate formula (styrene)-$(SO_3^-)[\{[(CH_3)_2NC_6H_4]_3P\}(CH_3^+)]$.

EXAMPLE 11

Preparation of phosphonated styrene-divinylbenzene resin/methylquaternized ($[(CH_3)_2NC_6H_4]_3P$) compound.

This material was prepared in a manner similar to Example 10 except that 5.0 g of Bio-Rex 63 (microreticular gel), phosphonated, 6.6 meq/g) was used. Analysis showed the product as having the approximate formula (styrene-divinylbenzene)-$(PO_3^-)[\{[(CH_3)_2NC_6H_4]_3P\}(CH_3^+)]$.

EXAMPLE 12

Preparation of carboxylated acrylic resin/methylquaternized ($[(CH_3)_2NC_6H_4]_3P$).

This material was prepared in a manner similar to Example 10 except that 5.0 g of Bio-Rex 70 (acrylic polymer, carboxylic acid exchange group, 10.2 meq/g) was used. Analysis showed the product as having the approximate formula acrylic-$(CO_2^-)[\{[(CH_3)_2NC_6H_4]_3P\}(CH_3^+)]$.

EXAMPLE 13

Preparation of vinyl pyridinium resin/$[o\text{-}O_2CC_6H_4P(C_6H_5)_2]$ compound.

A 10 g portion of Bio-Rex 9 (100–200 mesh, polymerized vinylpyridine, pyridinium type, 3.7 meq/g) was placed in a course grade fritted glass funnel and treated with 1 liter of 0.1 N HCl in the manner described in Example 10. The resin was then rinsed with 2 liters of deionized water, and finally with acetone. The resin was then dried for 2 days at about 40° C. in a vacuum oven.

A 5.0 g portion of resin was then added to about 500 ml of $H_2O$ in a round bottom flask. A 1.29 g (3.8 mmol) of diphenyl-(2-carboxyphenyl)phosphine was placed in a small flask of $H_2O$/acetone (5.0 g $H_2O$, 5.0 ml acetone) with 0.15 g of dissolved NaOH. After the phosphine was dissolved, the solution of phosphine was added to the solution which contained the resin. This was stirred overnight under an $N_2$ atmosphere. The material was filtered and washed with a 50—50 v/v mix of acetone/water and finally with acetone. Analysis showed the product having the approximate formula (ethylene)-(pyridinium$^+$) $[o\text{-}O_2CC_6H_4P(C_6H_5)_2^-]$.

EXAMPLE 14

Preparation of quaternary ammonium styrene-divinylbenzene resin/$(HO_2CC_5H_4 N)$ compound.

To a solution of NaOH (1.5 g) in 150 ml of deionized $H_2O$ was added 4.6 g (38.4 mmol) of isonicotinic acid. To the resultant solution was added 6.0 g of Bio-Rad AG-1 (styrene-divinylbenzene microreticular anion-exchange resin, Cl-form, 20–50 mesh, 3.2 meq/g), side-stirred for 2 hours, and filtered by suction. The resin material was then washed with 3×50 ml of acetone, and dried in vacuum oven (45° C.). Analysis showed a product having the approximate formula (styrene-divinylbenzene)-$[CH_2N^+(CH_3)_3](^-O_2CC_5H_4N)$.

EXAMPLE 15

Preparation of quaternary ammonium styrene resin/$(HO_2CC_5H_4N)$.

This material was prepared in a similar manner as in Example 14 except that 5.9 g (48.0 mmol) of isonicotinic acid and 6.0 g of the Dow MSA-1 (macroreticular polystyrene base-quaternary exchange group, 4.0 meq/g) resin were used. Analysis showed a product having the approximate formula (styrene)-$[CH_2N^+(CH_3)_3](^-O_2CC_5H_4N)$.

PREPARATION OF RESIN-LINKING COMPOUND-METAL COMPLEX COMPOSITIONS

EXAMPLE 16

Preparation of sulfonated styrene-divinylbenzene resin/methylquaternized ($[(CH_3)_2NC_6H_4]_3P$)/molybdenum-complex composition.

To a 1-liter flask was added 1.74 g $Mo(NO)_2Cl_2$, 50 ml of methanol, and 15 g of aminophosphine/resin material prepared as described in Example 6. The mixture was stirred for 24 hours, the solid filtered and washed with methanol and dried under vacuum. Analysis showed the composition as having the approximate formula (styrene-divinylbenzene)-$(SO_3^-)_x[\{[(CH_3)_2NC_6H_4]_3P\}(CH_3^+)]_x]Mo(NO)_{2-x}Cl_{0.4}]_{0.3}$ where $x=1$ or 2.

PROCESS UTILIZING COMPOSITIONS ACCORDING TO THIS INVENTION

EXAMPLE 17

Olefin Metathesis (Disproportionation) Process

To a mixture of 4 ml of chlorobenzene, 2 ml of 1-hexene, 1.0 g of the resin/ligand/molybdenum composition prepared as described in Example 16 was added 200 ml of 25% $Al_2(CH_3)_3Cl_3$ in hexane. The mixture was stirred for 2 hours at room temperature. Analysis showed a 4.7% yield of decenes after 2 hours.

EXAMPLE 18

Repeating the disproportionation process of Example 17 with an $Al(CH_3CH_2)_2Cl$ activator showed a 10% metathesis conversion, but no decenes, after 15 minutes.

Illustrative Example 19

Repeating the disproportionation process of Example 17 with resin/ligand/tungsten and resin/ligand/rhenium catalyst prepared similar to Example 16 will produce significant amounts of decenes.

Illustrative Example 20

Repeating the disproportionation process of Example 17 with a $(CH_3)_4Sn$ activator will produce significant amounts of decenes.

What is claimed is:

1. A process for the production of olefins by disproportionation which comprises contacting at a temperature of between about $-20°$ C. and $+150°$ C. and a pressure of between about 0 and 2000 psig an olefinic hydrocarbon feedstock capable of undergoing a disproportionation process with an activator and a catalyst comprising:

(a) an ion exchange resin;

(b) a metal selected from the group consisting of molybdenum, tungsten and rhenium; and (c) an organic linking compound which has at least one moiety which is ionically bonded to said ion exchange resin and further has at least one moiety which is coordinately bonded to said metal.

2. The process of claim 1 where, in the catalyst, the ion exchange resin is a strongly acidic, weakly acid or mixed acid-base type and the linking compound contains from 1 to about 100 carbon atoms, the ionically bonded moiety of the linking compound is selected from the group consisting of monohydrocarbyl ammonium, dihydrocarbyl ammonium, trihydrocarbyl ammonium, quaternary ammonium, pyridinium, phosphonium, arsonium and sulfonium ion and the coordinately bonded moiety contains a heteroatom selected from the group consisting of trivalent nitrogen, trivalent phosphorus, trivalent arsenic, trivalent bismuth and trivalent antimony.

3. The process of claim 2 where, in the catalyst, the ion exchange resin has a functional group selected from the group consisting of sulfonic acid, fluorinated alkyl sulfonic acid, phosphonic acid, carboxylic acid and aminocarboxylic acid, the ionically bonded moiety is selected from the group consisting of monohydrocarbyl ammonium, dihydrocarbyl ammonium, trihydrocarbyl ammonium, quaternary ammonium, pyridinium and phosphonium and the coordinately bonded moiety contains a heteroatom selected from the group consisting of trivalent nitrogen and trivalent phosphorus.

4. The process of claim 3 where, in the catalyst, the ion exchange resin has a backbone selected from the group consisting of polymerized sytrene, styrene-divinylbenzene, phenol-formaldehyde, benzene-formaldehyde, acrylic acid and methacrylic acid.

5. The process of claim 4 where, in the catalyst, the metal is selected from the group consisting of molybdenum and tungsten.

6. The process of claim 1 where, in the catalyst, the ion exchange resin is a basic-type resin, the linking compound contains from 1 to about 100 carbon atoms, the ionically bonded moiety of the linking compound is derived from the group consisting of carboxylic acid, phosphonic acid, phosphinic acid, sulfenic acid, sulfinic acid, sulfonic acid, boronic acid and boronous acid and the coordinately bonded moiety contains a heteroatom selected from the group consisting of trivalent nitrogen, trivalent phosphorus, trivalent arsenic, trivalent bismuth and trivalent antimony.

7. The process of claim 6 where, in the catalyst, the ion exchange resin has a functional group selected from the group consisting of primary, secondary, tertiary, quaternary amine and pyridinium and the ionically bonded moiety is selected from the group consisting of trivalent nitrogen and trivalent phosphorus.

8. The process of claim 7 where, in the catalyst, the ion exchange resin has a backbone selected from the group consisting of polymerized styrene, styrene-divinylbenzene, phenol-formaldehyde, benzene-formaldehyde, epoxypolyamine and phenolic-polyamine.

9. The process of claim 8 where, in the catalyst, the metal is selected from the group consisting of molybdenum and tungsten.

10. The process of claim 1, where the activator comprises a compound selected from the group consisting of compounds having the general formula $r_v T g_w$ wherein r is independently selected from the group consisting of hydrogen, hydrocarbyl radicals, and the halogenated and oxygenated derivatives thereof, said activator containing up to 30 carbon atoms, T is selected from the group consisting of Group I to III and IVA metals, g is a halogen radical, v is an integer of from 0 to 4, and w is an integer of from 0 to 4, v and w having a total equal to the valence of T.

11. The process of claim 10 where, in the activator, the metal is selected from the group consisting of aluminum and tin.

12. The process of claim 11, where the activator is selected from the group consisting of $Al(CH_3CH_2)_2Cl$, $Al_2(CH_3)_3Cl_3$, $(CH_3)_4Sn$ and $AlCl_3$.

13. The process of claim 12, where the activator is selected from the group consisting of $Al(CH_3CH_2)_2 Cl$ and $Al_2(CH_3)_3Cl_3$.

* * * * *